United States Patent
Muramatsu et al.

(10) Patent No.: US 8,524,472 B2
(45) Date of Patent: Sep. 3, 2013

(54) METHOD FOR PRODUCING 2-BUTANOL AND RECOMBINANT MICROORGANISM HAVING 2-BUTANOL PRODUCTION CAPACITY

(75) Inventors: Masayoshi Muramatsu, Miyoshi (JP); Kazuyo Suzuki, Toyota (JP)

(73) Assignee: Toyota Jidosha Kabushiki Kaisha, Aichi (JP)

( * ) Notice: Subject to any disclaimer, the term of this patent is extended or adjusted under 35 U.S.C. 154(b) by 97 days.

(21) Appl. No.: 13/104,600

(22) Filed: May 10, 2011

(65) Prior Publication Data

US 2011/0281315 A1 Nov. 17, 2011

(30) Foreign Application Priority Data

May 14, 2010 (JP) ................................. 2010-112405

(51) Int. Cl.
| | | |
|---|---|---|
| *C12P 7/16* | (2006.01) | |
| *C12N 9/00* | (2006.01) | |
| *C12N 1/00* | (2006.01) | |
| *C12N 1/20* | (2006.01) | |
| *C12N 15/00* | (2006.01) | |
| *C07H 21/04* | (2006.01) | |

(52) U.S. Cl.
USPC ........ 435/160; 435/183; 435/243; 435/252.3; 435/320.1; 536/23.2

(58) Field of Classification Search
None
See application file for complete search history.

(56) References Cited

U.S. PATENT DOCUMENTS

2007/0265477 A1   11/2007   Gupta et al.

FOREIGN PATENT DOCUMENTS

| JP | 2007-535964 A | 12/2007 |
| WO | 2008/098227 A2 | 8/2008 |
| WO | 2008/137403 A1 | 11/2008 |

OTHER PUBLICATIONS

Accession ARL19400, Jun. 12, 2008.*
Accession U08465, Dec. 4, 1995.*
Accession A5I5T2, Jun. 26, 2007.*
Petersen et al. Appl Environ Microbiol. Nov. 1990;56(11):3491-8.*
Accession P25984, May 1, 1992.*
Chica et al. Curr Opin Biotechnol. Aug. 2005;16(4):378-84.*
Sen et al. Appl Biochem Biotechnol. Dec. 2007;143(3):212-23.*

* cited by examiner

*Primary Examiner* — Christian Fronda
(74) *Attorney, Agent, or Firm* — Sughrue Mion, PLLC

(57) ABSTRACT

This invention is intended to produce 2-butanol with excellent productivity via a fermentation process. Recombinant microorganisms into which the acetoacetyl-CoA synthase gene and a group of genes (i.e., genes involved in 2-propanol synthesis) encoding a set of enzymes synthesizing 2-propanol from acetoacetyl-CoA have been introduced are cultured, so that, in addition to 2-propanol, 2-butanol is produced at a high level in a medium.

13 Claims, 4 Drawing Sheets

SEQUENCE LISTING

```
<160> NUMBER OF SEQ ID NOS: 21

<210> SEQ ID NO 1
<211> LENGTH: 329
<212> TYPE: PRT
<213> ORGANISM: Streptomyces sp.

<400> SEQUENCE: 1

Met Thr Asp Val Arg Phe Arg Ile Ile Gly Thr Gly Ala Tyr Val Pro
1               5                   10                  15

Glu Arg Ile Val Ser Asn Asp Glu Val Gly Ala Pro Ala Gly Val Asp
            20                  25                  30

Asp Asp Trp Ile Thr Arg Lys Thr Gly Ile Arg Gln Arg Arg Trp Ala
        35                  40                  45

Ala Asp Asp Gln Ala Thr Ser Asp Leu Ala Thr Ala Ala Gly Arg Ala
    50                  55                  60

Ala Leu Lys Ala Ala Gly Ile Thr Pro Glu Gln Leu Thr Val Ile Ala
65                  70                  75                  80

Val Ala Thr Ser Thr Pro Asp Arg Pro Gln Pro Pro Thr Ala Ala Tyr
                85                  90                  95

Val Gln His His Leu Gly Ala Thr Gly Thr Ala Ala Phe Asp Val Asn
            100                 105                 110

Ala Val Cys Ser Gly Thr Val Phe Ala Leu Ser Ser Val Ala Gly Thr
        115                 120                 125

Leu Val Tyr Arg Gly Gly Tyr Ala Leu Val Ile Gly Ala Asp Leu Tyr
    130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
            180                 185                 190

Leu Ile Arg Val Pro Ala Gly Gly Ser Arg Gln Pro Leu Asp Thr Asp
        195                 200                 205

Gly Leu Asp Ala Gly Leu Gln Tyr Phe Ala Met Asp Gly Arg Glu Val
    210                 215                 220

Arg Arg Phe Val Thr Glu His Leu Pro Gln Leu Ile Lys Gly Phe Leu
225                 230                 235                 240

His Glu Ala Gly Val Asp Ala Ala Asp Ile Ser His Phe Val Pro His
                245                 250                 255

Gln Ala Asn Gly Val Met Leu Asp Glu Val Phe Gly Glu Leu His Leu
            260                 265                 270

Pro Arg Ala Thr Met His Arg Thr Val Glu Thr Tyr Gly Asn Thr Gly
        275                 280                 285

Ala Ala Ser Ile Pro Ile Thr Met Asp Ala Ala Val Arg Ala Gly Ser
    290                 295                 300
```

```
Phe Arg Pro Gly Glu Leu Val Leu Ala Gly Phe Gly Gly Gly Met
305                 310                 315                 320

Ala Ala Ser Phe Ala Leu Ile Glu Trp
                325

<210> SEQ ID NO 2
<211> LENGTH: 392
<212> TYPE: PRT
<213> ORGANISM: Clostridium acetobutylicum

<400> SEQUENCE: 2

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
                20                  25                  30

Ala Ile Lys Glu Ala Val Lys Lys Ala Gly Ile Lys Pro Glu Asp Val
                35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
                100                 105                 110

Gly Gly Met Glu Asn Met Ser Arg Ala Pro Tyr Leu Ala Asn Asn Ala
            115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
                180                 185                 190

Gly Gln Phe Lys Asp Glu Ile Val Pro Val Val Ile Lys Gly Arg Lys
            195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
                260                 265                 270

Ala Lys Ile Val Ser Tyr Gly Ser Ala Gly Val Asp Pro Ala Ile Met
            275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
                340                 345                 350
```

```
Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gln Gly
    370                 375                 380

Thr Ala Ile Leu Leu Glu Lys Cys
385                 390

<210> SEQ ID NO 3
<211> LENGTH: 218
<212> TYPE: PRT
<213> ORGANISM: Clostridium acetobutylicum

<400> SEQUENCE: 3

Met Asn Ser Lys Ile Ile Arg Phe Glu Asn Leu Arg Ser Phe Phe Lys
1               5                   10                  15

Asp Gly Met Thr Ile Met Ile Gly Gly Phe Leu Asn Cys Gly Thr Pro
                20                  25                  30

Thr Lys Leu Ile Asp Phe Leu Val Asn Leu Asn Ile Lys Asn Leu Thr
            35                  40                  45

Ile Ile Ser Asn Asp Thr Cys Tyr Pro Asn Thr Gly Ile Gly Lys Leu
        50                  55                  60

Ile Ser Asn Asn Gln Val Lys Lys Leu Ile Ala Ser Tyr Ile Gly Ser
65                  70                  75                  80

Asn Pro Asp Thr Gly Lys Lys Leu Phe Asn Asn Glu Leu Glu Val Glu
                85                  90                  95

Leu Ser Pro Gln Gly Thr Leu Val Glu Arg Ile Arg Ala Gly Gly Ser
            100                 105                 110

Gly Leu Gly Gly Val Leu Thr Lys Thr Gly Leu Gly Thr Leu Ile Glu
        115                 120                 125

Lys Gly Lys Lys Lys Ile Ser Ile Asn Gly Thr Glu Tyr Leu Leu Glu
130                 135                 140

Leu Pro Leu Thr Ala Asp Val Ala Leu Ile Lys Gly Ser Ile Val Asp
145                 150                 155                 160

Glu Ala Gly Asn Thr Phe Tyr Lys Gly Thr Thr Lys Asn Phe Asn Pro
                165                 170                 175

Tyr Met Ala Met Ala Ala Lys Thr Val Ile Val Glu Ala Glu Asn Leu
            180                 185                 190

Val Ser Cys Glu Lys Leu Glu Lys Glu Lys Ala Met Thr Pro Gly Val
        195                 200                 205

Leu Ile Asn Tyr Ile Val Lys Glu Pro Ala
        210                 215

<210> SEQ ID NO 4
<211> LENGTH: 221
<212> TYPE: PRT
<213> ORGANISM: Clostridium acetobutylicum

<400> SEQUENCE: 4

Met Ile Asn Asp Lys Asn Leu Ala Lys Glu Ile Ile Ala Lys Arg Val
1               5                   10                  15

Ala Arg Glu Leu Lys Asn Gly Gln Leu Val Asn Leu Gly Val Gly Leu
                20                  25                  30

Pro Thr Met Val Ala Asp Tyr Ile Pro Lys Asn Phe Lys Ile Thr Phe
            35                  40                  45

Gln Ser Glu Asn Gly Ile Val Gly Met Gly Ala Ser Pro Lys Ile Asn
        50                  55                  60
```

```
Glu Ala Asp Lys Asp Val Val Asn Ala Gly Gly Asp Tyr Thr Thr Val
 65                  70                  75                  80

Leu Pro Asp Gly Thr Phe Phe Asp Ser Ser Val Ser Phe Ser Leu Ile
                 85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
130                 135                 140

Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
                165                 170                 175

Glu Leu Gly Val Ile Glu Val Ile Asn Asp Gly Leu Leu Leu Thr Glu
            180                 185                 190

Ile Asn Lys Asn Thr Thr Ile Asp Glu Ile Arg Ser Leu Thr Ala Ala
        195                 200                 205

Asp Leu Leu Ile Ser Asn Glu Leu Arg Pro Met Ala Val
    210                 215                 220

<210> SEQ ID NO 5
<211> LENGTH: 244
<212> TYPE: PRT
<213> ORGANISM: Clostridium acetobutylicum

<400> SEQUENCE: 5

Met Leu Lys Asp Glu Val Ile Lys Gln Ile Ser Thr Pro Leu Thr Ser
  1               5                  10                  15

Pro Ala Phe Pro Arg Gly Pro Tyr Lys Phe His Asn Arg Glu Tyr Phe
                 20                  25                  30

Asn Ile Val Tyr Arg Thr Asp Met Asp Ala Leu Arg Lys Val Val Pro
             35                  40                  45

Glu Pro Leu Glu Ile Asp Glu Pro Leu Val Arg Phe Glu Ile Met Ala
         50                  55                  60

Met His Asp Thr Ser Gly Leu Gly Cys Tyr Thr Glu Ser Gly Gln Ala
 65                  70                  75                  80

Ile Pro Val Ser Phe Asn Gly Val Lys Gly Asp Tyr Leu His Met Met
                 85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Asp Tyr Gly Lys Leu Arg Val Ala Thr Ala Thr
130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205
```

```
Ala Met Ala Pro Leu Asn Asp Leu Pro Val Lys Glu Ile Val Ser Ser
        210                 215                 220

Ser His Ile Leu Ala Asp Ile Ile Leu Pro Arg Ala Glu Val Ile Tyr
225                 230                 235                 240

Asp Tyr Leu Lys

<210> SEQ ID NO 6
<211> LENGTH: 351
<212> TYPE: PRT
<213> ORGANISM: Clostridium beijerinckii

<400> SEQUENCE: 6

Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285

Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320
```

```
Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
        340                 345                 350

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 7
atgaaagaag ttgtaatagc tagtgcag                                    28

<210> SEQ ID NO 8
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 8
ctagcacttt tctagcaata ttgctg                                      26

<210> SEQ ID NO 9
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 9
aaacatatga agaagttgt aatagc                                       26

<210> SEQ ID NO 10
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 10
aaactcgagc tagcactttt ctagcaat                                    28

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 11
aaacatatga ccgacgtccg attccgcat                                   29

<210> SEQ ID NO 12
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 12
aaactcgagt taccactcga tcagggcga                                   29
```

```
<210> SEQ ID NO 13
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 13
attcatatga actctaaaat aattagattt gaaaatttaa ggtc                    44

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
agactcgagc taaacagcca tgggtctaag                                    30

<210> SEQ ID NO 15
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 15
cacgtcgaca aggagatata atgttaaagg atgaagtaat taaaca                  46

<210> SEQ ID NO 16
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 16
cacgcggccg cttacttaag ataatcatat ataacttcag c                       41

<210> SEQ ID NO 17
<211> LENGTH: 1097
<212> TYPE: DNA
<213> ORGANISM: Artificial Sequence
<220> FEATURE:
<223> OTHER INFORMATION: Synthetic polynucleotide

<400> SEQUENCE: 17
cgggtttccg cggtctagag ccaccatgaa aggtttcgca atgttgggta tcaataagtt    60
aggctggata gagaaagaaa gacctgtcgc aggtagctat gatgccattg ttcgaccatt   120 agccgttttct ccttgcacat ccgacattca cacagtgttt gaaggtgcat taggagatag   180
gaagaacatg atactgggtc atgaagccgt cggagaagta gttgaagttg aagcgaagt    240 aaaggacttt aagcctggtg atagagtgat cgttccttgc acaactccag attggagatc   300
attagaagtt caagctggat tccaacagca ttctaatggc atgcttgctg gttggaaatt   360
cagtaatttc aaggatggcg tgtttggtga gtactttcat gtcaatgatg cagatatgaa   420
cctagctatt cttcccaagg atatgccatt ggagaatgct gtcatgataa ccgacatgat   480
gactactggg tttcatggtg ctgaactagc ggacattcag atgggttcat cggttgttgt   540
gattggtatt ggtgctgttg gacttatggg gattgcaggc gcaaaattgc gtggtgccgg   600
ccgtatcatt ggcgtaggtt cgagacccat atgtgtggaa gctgcgaaat tctatgtgc    660 tacagacatt ttgaactaca agaatggtca catagttgac caagtcatga aactgaccaa   720
```

```
tgggaaaggc gttgataggg tgattatggc tggtggtgga tctgaaactt tgagtcaagc        780
cgtctctatg gtaaaaccag gtggaatcat atccaatatc aactaccatg ggtcaggaga        840
tgcgttactt ataccgagag ttgagtgggg atgtggcatg gcacacaaaa cgattaaggg        900
tggtttatgt ccaggcggaa gattaagagc tgaaatgtta agagatatgg ttgtatataa        960
cagggttgat ctgtccaaac tagtgacgca tgtatatcac gggtttgatc atatcgagga       1020
agcattgttg ttgatgaaag ataaaccgaa agacctaatc aaggccgtag tcattttgta       1080
aggatccgtc gacgggg                                                      1097

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
ggggtttccg cggtctagag ccacc                                               25

<210> SEQ ID NO 19
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 19
ggatccgtcg acgggg                                                         16

<210> SEQ ID NO 20
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 20
ggaattccat gaaaggtttc gcaatgtt                                            28

<210> SEQ ID NO 21
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 21
aactgcagaa ccaatgcatt ggttacaaaa tgactacgg                                39
```

METHOD FOR PRODUCING 2-BUTANOL AND RECOMBINANT MICROORGANISM HAVING 2-BUTANOL PRODUCTION CAPACITY

BACKGROUND OF THE INVENTION

1. Field of the Invention

The present invention relates to a method for producing butanol using a recombinant microorganism having butanol production capacity, into which genes involved in 2-butanol (or sec-butyl alcohol) biosynthesis have been incorporated, and a recombinant microorganism.

2. Background Art

In recent years, depletion of petroleum resources and global reduction of carbon dioxide emissions have been actively discussed. It is predicted that the petroleum prices will sharply increase in the future. Therefore, development of alternative petroleum materials has been awaited. For example, there have been attempts to bioconvert biomass, sugar, starch, fat and oil, proteins, and the like, which have been produced by plants from water and carbon dioxide, into alternative petroleum materials with the use of solar energy for practical use. An example of such an attempt is the development of the technology of producing plant-derived polylactic acid or polybutylene succinate as alternative plastic materials made from petroleum. Further, ethanol is obtained via fermentative production from sugar, starch, or the like and blended with automobile fuel purified from petroleum so as to be used in the U.S.A., Brazil, and other countries.

In addition, 2-butanol is an important compound that can be used for either fuel or resin material. 2-Butanol is an important substance as a starting material for high-octane automobile fuel or for resin such as propylene. In the past, 2-butanol had been synthesized using petroleum as a starting material. In view of petroleum depletion and the increased amount of $CO_2$ emitted into the air, 2-butanol synthesis via a fermentation process has been desired.

US 2007/0265477 discloses a method for synthesizing 2-butanol from 2-butanone with the use of a carbonyl reductase. WO 2008/098227 discloses a method for synthesizing 2,3-butanediol via a fermentation process and then chemically converting 2,3-butanediol into 2-butanol. Further, WO 2008/137403 discloses a method for directly synthesizing 2-butanol from 2,3-butanediol via a fermentation process.

According to the method disclosed by US 2007/0265477, however, highly purified 2-butanol cannot be obtained because ketones are simultaneously generated. The enzyme reaction of a carbonyl reductase disclosed by US 2007/0265477 requires the use of NADH, which is difficult to mass-produce and is very expensive. A secondary alcohol may be added to the reaction system and NADH resulting from an oxidation reaction thereof may be used. Such method, however, may suffer from the problem of contamination with an alcohol other than the target 2-butanol and an oxide of such alcohol.

The method disclosed by WO 2008/098227 requires the use of a catalyst containing rare metals such as platinum or rubidium at high concentrations (e.g., 5% by weight) in the reaction system. In addition, the method requires the use of a hydrogenation catalyst and an acid catalyst for the entire reaction. According to the method disclosed by WO 2008/098227, the efficiency for chemical conversion into 2-butanol is about 70% at most. That is, this method is disadvantageously low in productivity.

According to the method disclosed by WO 2008/137403, acetolactic acid synthesized from the two pyruvic acid molecules generated in the glycolytic pathway is converted into 2-butanol through acetoin, 2,3-butanediol, and 2-butanone. That is, this method involves many reaction steps and thus is poor in productivity.

SUMMARY OF THE INVENTION

Object of the Invention

Under the above circumstances, it is an object of the present invention to provide a method for producing 2-butanol with excellent productivity via a fermentation process. It is another object to provide a recombinant microorganism having excellent capacity for 2-butanol production.

Means for Attaining the Object

The present inventors have conducted concentrated studies in order to attain the above objects. As a result, surprisingly, they discovered that, along with 2-propanol, 2-butanol would be produced at a high level via culture of recombinant microorganisms into which the acetoacetyl-CoA synthase gene and genes (i.e., genes involved in 2-propanol synthesis) encoding a group of enzymes synthesizing 2-propanol from acetoacetyl-CoA have been introduced. This has led to the completion of the present invention. The present invention includes the following.

(1) A method for producing 2-butanol comprising culturing a recombinant microorganism into which an acetoacetyl-CoA synthase gene and a group of genes involved in 2-propanol biosynthesis associated with a metabolic pathway that synthesizes 2-propanol from acetoacetyl-CoA have been introduced and obtaining 2-butanol from the culture product.

(2) The method for producing 2-butanol according to (1), wherein the acetoacetyl-CoA synthase gene encodes an enzyme that catalyzes a reaction that converts two acetyl-CoA molecules into acetoacetyl-CoA.

(3) The method for producing 2-butanol according to (2), wherein the acetoacetyl-CoA synthase gene is the thiolase gene (the thlA gene) derived from *Clostridium acetobutylicum*.

(4) The method for producing 2-butanol according to (3), wherein the acetoacetyl-CoA synthase gene encodes a protein comprising the amino acid sequence of SEQ ID NO: 2 or a protein comprising an amino acid sequence having 80% or higher identity to the amino acid sequence of SEQ ID NO: 2 and having a function of synthesizing acetoacetyl-CoA from two acetyl-CoA molecules.

(5) The method for producing 2-butanol according to (1), wherein the acetoacetyl-CoA synthase gene encodes an enzyme that catalyzes a reaction that converts acetyl-CoA and malonyl-CoA into acetoacetyl-CoA.

(6) The method for producing 2-butanol according to (5), wherein the acetoacetyl-CoA synthase gene is a gene (the orfN gene) derived from a *Streptomyces* microorganism.

(7) The method for producing 2-butanol according to (6), wherein the acetoacetyl-CoA synthase gene encodes a protein comprising the amino acid sequence of SEQ ID NO: 1 or a protein comprising an amino acid sequence having 80% or higher identity to the amino acid sequence of SEQ ID NO: 1 and having a function of synthesizing acetoacetyl-CoA from malonyl-CoA and acetyl-CoA.

(8) The method for producing 2-butanol according to (1), wherein the group of genes involved in 2-propanol biosynthesis consists of the acetoacetyl-CoA transferase gene, the acetoacetic acid decarboxylase gene, and the isopropanol dehydrogenase gene, and the recombinant microorganism is obtained via introduction of genes selected from among the group of genes involved in 2-propanol biosynthesis, wherein the genes to be introduced are not exist in the microorganism as an endogenous gene.

(9) The method for producing 2-butanol according to (8), wherein the acetoacetyl-CoA transferase gene is the ctfA or ctfB gene derived from *Clostridium acetobutylicum*.

(10) The method for producing 2-butanol according to (8) or (9), wherein the acetoacetic acid decarboxylase gene is the adc gene derived from *Clostridium acetobutylicum*.

(11) The method for producing 2-butanol according to any of (8) to (10), wherein the isopropanol dehydrogenase gene is the pdh gene derived from *Clostridium beijerinckii*.

(12) The method for producing 2-butanol according to (1), wherein the recombinant microorganism is obtained from an *E. coli* host strain.

(13) The method for producing 2-butanol according to (12), wherein the *E. coli* strain is an *E. coli* K strain.

(14) A recombinant microorganism into which the acetoacetyl-CoA synthase gene (the orfN gene) derived from a *Streptomyces* microorganism and a group of genes involved in 2-propanol biosynthesis associated with a metabolic pathway for synthesizing 2-propanol from acetoacetyl-CoA have been introduced.

(15) The recombinant microorganism according to (14), wherein the acetoacetyl-CoA synthase gene encodes a protein comprising the amino acid sequence of SEQ ID NO: 1 or a protein comprising an amino acid sequence having 80% or higher identity to the amino acid sequence of SEQ ID NO: 1 and having a function of synthesizing acetoacetyl-CoA from malonyl-CoA and acetyl-CoA.

(16) The recombinant microorganism according to (14), wherein the group of genes involved in 2-propanol biosynthesis consists of the acetoacetyl-CoA transferase gene, the acetoacetic acid decarboxylase gene, and the isopropanol dehydrogenase gene, and genes selected from among the group of genes involved in 2-propanol biosynthesis has been introduced, wherein the genes to be introduced are not exist in the microorganism as an endogenous gene.

(17) The recombinant microorganism according to (16), wherein the acetoacetyl-CoA transferase gene is the ctfA or ctfB gene derived from *Clostridium acetobutylicum*.

(18) The recombinant microorganism according to (16) or (17), wherein the acetoacetic acid decarboxylase gene is the adc gene derived from *Clostridium acetobutylicum*.

(19) The recombinant microorganism according to (16) or (17), wherein the isopropanol dehydrogenase gene is the pdh gene derived from *Clostridium beijerinckii*.

(20) The recombinant microorganism according to (14), which is obtained from an *E. coli* host strain.

(21) The recombinant microorganism according to (20), wherein the *E. coli* strain is an *E. coli* K strain.

Effects of the Invention

The present invention can provide a method for producing 2-butanol with excellent productivity with the use of a recombinant microorganism having 2-butanol production capacity. According to the method for producing 2-butanol of the present invention, specifically, productivity of 2-butanol used for a fuel or a resin material can be improved, and the cost of butanol production can be reduced.

Also, the recombinant microorganism of the present invention has a capacity for butanol production superior to that of a conventional recombinant microorganism having butanol production capacity.

EMBODIMENTS OF THE INVENTION

Figure 1:
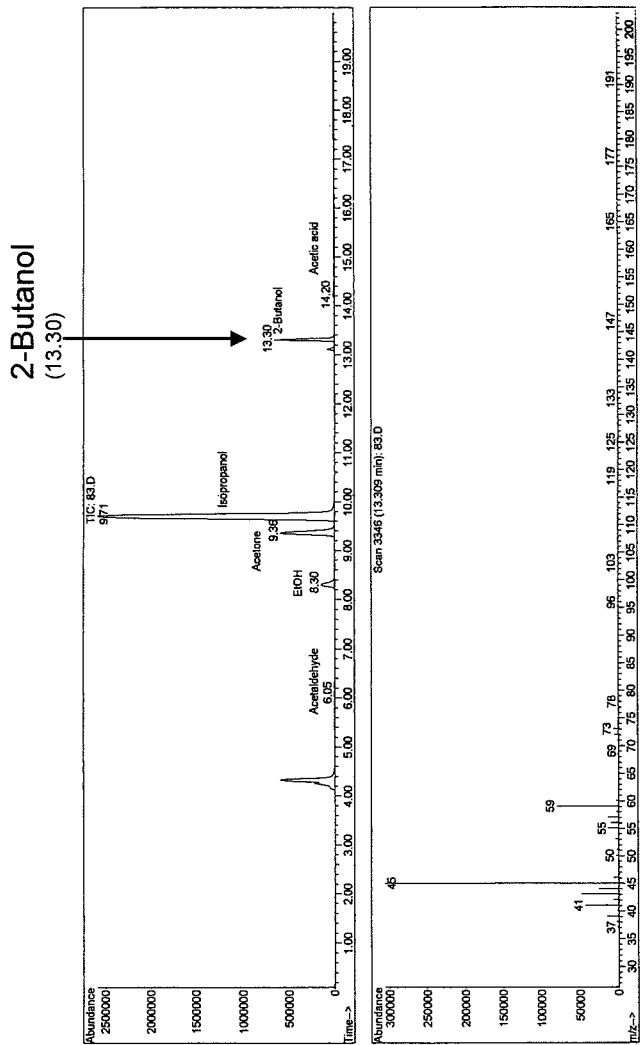
FIG. 1 is a characteristic diagram showing the results of GC-MS analysis of the culture solution of a recombinant *E. coli* strain.

Hereafter, the present invention is described in detail.

The method for producing 2-butanol (or sec-butyl alcohol) of the present invention comprises culturing a recombinant microorganism into which the acetoacetyl-CoA synthase gene and genes involved in 2-propanol biosynthesis associated with a metabolic pathway for synthesizing 2-propanol from acetoacetyl-CoA have been introduced and obtaining 2-butanol from the culture product.

Acetoacetyl-CoA Synthase Gene

The acetoacetyl-CoA synthase gene encodes an enzyme having activity of synthesizing acetoacetyl-CoA from malonyl-CoA and acetyl-CoA or an enzyme having activity of synthesizing acetoacetyl-CoA from two acetyl-CoA molecules. The enzyme having activity of synthesizing acetoacetyl-CoA from two acetyl-CoA molecules is occasionally referred to as "thiolase."

The gene encoding an acetoacetyl-CoA synthase having activity of synthesizing acetoacetyl-CoA from malonyl-CoA and acetyl-CoA has been found in, for example, an actinomycete of the genus *Streptomyces* (JP Patent Publication (Kokai) No. 2008-61506 A). For example, a gene derived from an actinomycete of the genus *Streptomyces* can be used.

An example of such an acetoacetyl-CoA synthase gene is a gene encoding a protein having the amino acid sequence of SEQ ID NO: 1. Such a protein having the amino acid sequence of SEQ ID NO: 1 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules, and it has been found in an actinomycete of the *Streptomyces* sp. CL190 strain (JP Patent Publication (Kokai) No. 2008-61506 A).

The gene encoding a protein having the amino acid sequence of SEQ ID NO: 1 can be obtained by a nucleic acid amplification method (e.g., PCR) with the use of genomic DNA obtained from an actinomycete of the *Streptomyces* sp. CL190 strain as a template and a pair of primers that was designed with reference to JP Patent Publication (Kokai) No. 2008-61506 A.

As a gene encoding an acetoacetyl-CoA synthase (thiolase) having activity of synthesizing acetoacetyl-CoA from two acetyl-CoA molecules, a known gene, which is the acetoacetyl-CoA synthase gene identified in various organisms, can be used. The acetoacetyl-CoA synthase gene is involved in a mevalonic acid pathway existing in a variety of organism species.

An example thereof is the thiolase gene derived from *Clostridium acetobutylicum* (deposited under the accession number ATCC824). The thiolase gene derived from *Clostridium acetobutylicum* is denoted by the thlA gene, and it encodes a protein having the amino acid sequence of SEQ ID NO: 2. Examples of the thiolase genes that can be used include genes derived from *Schizosaccharomyces pombe, Saccharomyces cerevisiae, Escherichia coli, Macaca mulatta, Bos taurus, Drosophila melanogaster, Oryza sativa, Aspergillus oryzae, Bacillus amyloliquefaciens,* and *Clostridium kluyveri.*

In the present invention, the acetoacetyl-CoA synthase gene is not limited to a gene encoding a protein having an amino acid sequence of SEQ ID NO: 1 derived from the *Streptomyces* sp. CL190 strain, and it may be a gene encoding a protein comprising an amino acid sequence highly similar to the amino acid sequence of SEQ ID NO: 1 and having the function of synthesizing acetoacetyl-CoA from malonyl-CoA and acetyl-CoA. In the present invention, the acetoacetyl-CoA synthase gene is not limited to a thiolase gene encoding a protein having the amino acid sequence of SEQ ID NO: 2 derived from *Clostridium acetobutylicum*, and it may be a gene encoding a protein comprising an amino acid sequence highly similar to the amino acid sequence of SEQ ID NO: 2 and having the function of synthesizing acetoacetyl-CoA from two acetyl-CoA molecules. The expression "highly similar" used herein refers to, for example, 80% or higher identity, preferably 90% or higher identity, more preferably 95% or higher identity, and most preferably 97% or higher identity. Herein, the identity value corresponds to the percentage of amino acid residues in the amino acid sequence of SEQ ID NO: 1 or 2 and another amino acid sequence that are identical, and it is calculated by aligning the amino acid sequence of SEQ ID NO: 1 or 2 with another amino acid sequence, with the use of a program for searching for sequence similarity (occasionally referred to as the "homology search program").

In the present invention, the acetoacetyl-CoA synthase gene may be a gene encoding a protein having an amino acid sequence derived from the amino acid sequence of SEQ ID NO: 1 by substitution, deletion, addition, or insertion of 1 or more amino acids and having the function of synthesizing acetoacetyl-CoA from malonyl-CoA and acetyl-CoA. In the present invention, further, the acetoacetyl-CoA synthase gene may be a gene encoding a protein having an amino acid sequence derived from the amino acid sequence of SEQ ID NO: 2 by substitution, deletion, addition, or insertion of 1 or more amino acids and having the function of synthesizing acetoacetyl-CoA from two acetyl-CoA molecules. Herein, the expression "more amino acids" refers to, for example, 2 to 30 amino acids, preferably 2 to 20 amino acids, more preferably 2 to 10 amino acids, and most preferably 2 to 5 amino acids.

In the present invention, the acetoacetyl-CoA synthase gene may be a polynucleotide hybridizing to a portion or the entirety of a polynucleotide having a nucleotide sequence complementary to the nucleotide sequence encoding the amino acid sequence of SEQ ID NO: 1 under stringent conditions and encoding a protein having the function of synthesizing acetoacetyl-CoA from malonyl-CoA and acetyl-CoA. In the present invention, further, the acetoacetyl-CoA synthase gene may be a polynucleotide hybridizing to a portion or the entirety of a polynucleotide having a nucleotide sequence complementary to the nucleotide sequence encoding the amino acid sequence of SEQ ID NO: 2 under stringent conditions and encoding a protein having the function of synthesizing acetoacetyl-CoA from two acetyl-CoA molecules. Herein, hybridization under stringent conditions takes place while binding is maintained during washing at 60° C. in 2×SSC. Hybridization can be carried out by conventionally known methods such as the method described in J. Sambrook et al., Molecular Cloning, A Laboratory Manual, 2nd Ed., Cold Spring Harbor Laboratory, 1989.

A gene encoding an acetoacetyl-CoA synthase having an amino acid sequence that differs from the amino acid sequence of SEQ ID NO: 1 as described above can be isolated from, for example, an actinomycete other than the *Streptomyces* sp. CL190 strain. Also, a gene encoding an acetoacetyl-CoA synthase having an amino acid sequence that differs from the amino acid sequence of SEQ ID NO: 2 can be isolated from, for example, *Clostridium* bacteria other than *Clostridium acetobutylicum* (ATCC824). In addition, such gene can be obtained by modifying a polynucleotide encoding the amino acid sequence of SEQ ID NO: 1 or 2 by a method known in the art. Mutagenesis of a nucleotide sequence can be carried out by a known method such as the Kunkel method or the gapped duplex method, or by a method similar to either thereof. For example, mutagenesis may be carried out with the use of a mutagenesis kit based on site-specific mutagenesis (e.g., Mutant-K and Mutant-G (trade names, TAKARA Bio)) or an LA PCR in vitro Mutagenesis series kit (trade name, TAKARA Bio).

The activity of an acetoacetyl-CoA synthase having an amino acid sequence that differs from the amino acid sequence of SEQ ID NO: 1 can be evaluated in the manner described below. Specifically, a gene encoding a protein to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of the reaction, the amount of substrate lost and/or the amount of product (acetoacetyl-CoA) produced are measured. This enables evaluation of whether or not the protein to be evaluated has the function of synthesizing acetoacetyl-CoA from malonyl-CoA and acetyl-CoA and evaluation of the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and measuring the amount of substrate lost and/or the amount of product produced in a similar manner.

The activity of an acetoacetyl-CoA synthase having an amino acid sequence that differs from the amino acid sequence of SEQ ID NO: 2 can be evaluated in the manner described below. Specifically, a gene encoding a protein to be evaluated is first introduced into a host cell such that the gene can be expressed therein, followed by purification of the protein by a technique such as chromatography. Acetyl-CoA is added as a substrate to a buffer containing the obtained protein to be evaluated, followed by, for example, incubation at a desired temperature (e.g., 10° C. to 60° C.). After the completion of the reaction, the amount of substrate lost and/or the amount of product (acetoacetyl-CoA) produced are measured. This enables evaluation of whether or not the protein to be evaluated has the function of synthesizing acetoacetyl-CoA from two acetyl-CoA molecules and evaluation of the degree of synthesis.

Group of Genes Involved in 2-Propanol Biosynthesis

The term "group of genes involved in 2-propanol biosynthesis" refers to a group consisting of a plurality of genes encoding enzymes associated with the metabolic pathway for biosynthesizing 2-propanol as a final product from acetoacetyl-CoA as a starting compound. Examples of enzymes associated with the metabolic pathway of 2-propanol biosynthesis include acetoacetyl-CoA transferase that synthesizes acetyl acetic acid using acetoacetyl-CoA as a substrate, acetoacetic acid decarboxylase that synthesizes acetone using acetyl acetic acid as a substrate, and isopropanol dehydrogenase that synthesizes 2-propanol using acetone as a substrate.

Genes encoding such enzymes can be isolated from microorganisms having 2-propanol biosynthesis capacity. Examples of microorganisms having 2-propanol biosynthesis capacity include, but are not limited to, bacteria. Examples of microorganisms having 2-propanol biosynthesis capacity include Clostridium microorganisms. Specific examples thereof include, but are not particularly limited to, Clostridium acetobutylicum, Clostridium beijerinckii, Clostridium saccharoperbutylacetonicum, Clostridium saccharoacetobutylicum, Clostridium aurantibutyricum, Clostridium pasteurianum, Clostridium sporogenes, Clostridium cadaveris, and Clostridium tetanomorphum. Use of genes involved in 2-propanol biosynthesis derived from Clostridium acetobutylicum and Clostridium beijerinckii, the full genome sequences of which have been analyzed, is particularly preferable.

In particular, the ctfA gene and the ctfB gene derived from Clostridium acetobutylicum can be used as acetoacetyl-CoA transferase genes. SEQ ID NO: 3 shows the amino acid sequence of a protein encoded by the ctfA gene and SEQ ID NO: 4 shows the amino acid sequence of a protein encoded by the ctfB gene. The adc gene derived from Clostridium acetobutylicum can be used as the acetoacetic acid decarboxylase gene. SEQ ID NO: 5 shows the amino acid sequence of a protein encoded by the adc gene. Further, the pdh gene derived from Clostridium beijerinckii can be used as the isopropanol dehydrogenase gene. SEQ ID NO: 6 shows the amino acid sequence of a protein encoded by the pdh gene.

Genes derived from, for example, Escherichia coli, Shigella sonnei, Pectobacterium carotovorum, Photorhabdus asymbiotica, Bacillus cereus, Citrobacter koseri, Streptococcus pyogenes, Clostridium difficile, and Clostridium beijerinckii can be used as acetoacetyl-CoA transferase (the α subunit) genes in addition to the ctfA gene described above. Also, genes derived from Escherichia coli, Citrobacter koseri, Haemophilus influenzae, Nitrobacter hamburgensis, Streptococcus pyogenes, Clostridium difficile, and Bacillus weihenstephanensis can be used as acetoacetyl-CoA transferase (the β subunit) genes in addition to the ctfB gene described above. In addition to the adc gene, genes derived from Saccharopolyspora erythraea, Streptomyces avermitilis, Bradyrhizobium sp., Rhizobium leguminosarum, Burkholderia mallei, Ralstonia solanacearum, Francisella tularensis, Clostridium botulinum, and Clostridium beijerinckii can be used as acetoacetic acid decarboxylase genes. In addition to the pdh gene, a gene derived from Rhodococcus ruber can be used as the isopropanol dehydrogenase gene.

In addition, the genes involved in 2-propanol biosynthesis are not limited to the genes described above. Genes homologous to the ctfA gene, the ctfB gene, and the adc gene derived from Clostridium acetobutylicum and a gene homologous to the pdh gene derived from Clostridium beijerinckii may be used. Such homologous genes can be identified via a homology search such as Blast or Fasta involving the use of a known algorithm in a database containing nucleotide sequences of genes and amino acid sequences of proteins. A homologous gene identified with the use of a database can be isolated from a microorganism by a known method so that it can be used. Specifically, nucleic acid fragments containing homologous genes can be obtained by a nucleic acid amplification method with the use of genomic DNA extracted from a microorganism as a template and primers designed based on the nucleotide sequences of the identified homologous genes.

Further, a cDNA library of the aforementioned microorganisms of the genus Clostridium having 2-propanol biosynthesis capacity is created by a known method, followed by identification of cDNAs that specifically hybridize to probes designed based on the nucleotide sequences of the ctfA gene, the ctfB gene, and the adc gene derived from Clostridium acetobutylicum and the pdh gene derived from Clostridium beijerinckii. Accordingly, the aforementioned homologous genes derived from microorganisms of the genus Clostridium having 2-propanol biosynthesis capacity can be obtained.

Methods for obtaining genes homologous to the ctfA gene, the ctfB gene, and the adc gene derived from Clostridium acetobutylicum and the pdh gene derived from Clostridium beijerinckii are not limited to the above methods, and any method can be used.

Transformation of a Host Microorganism

The aforementioned "acetoacetyl-CoA synthase gene" and "the genes involved in 2-propanol biosynthesis" are incorporated into an adequate expression vector and then introduced into a host microorganism. A host microorganism used herein is not particularly limited as long as it can express the genes of the present invention. Examples thereof include: bacteria belonging to the genus Escherichia (e.g., Escherichia coli), the genus Bacillus (e.g., Bacillus subtilis), the genus Pseudomonas (e.g., Pseudomonas putida), and the genus Rhizobium (e.g., Rhizobium meliloti); and yeasts such as Saccharomyces cerevisiae, Schizosaccharomyces pombe, and Pichia pastoris.

When a bacterium such as Escherichia coli is used as a host, it is preferable for an expression vector to be able to autonomously replicate in such bacterium and to be composed of a promoter, a ribosome binding sequence, the above gene, and a transcription termination sequence. In addition, such an expression vector may contain a gene that controls promoter activity.

As Escherichia coli, any conventionally known strain such as the Escherichia coli BL21 (DE3) strain, K12 strain, DH1 strain, or JM109 strain can be used. As Escherichia coli, use of a so-called K strain, such as the K12 strain or a strain prepared from the K12 strain, is particularly preferable. An example of Bacillus subtilis is the Bacillus subtilis 168 strain.

Any promoter may be used as long as it can be expressed in a host such as Escherichia coli. Examples of promoters that can be used include a trp promoter, a lac promoter, a PL promoter, a PR promoter derived from Escherichia coli, and a T7 promoter derived from a phage. Further, an artificially designed or modified promoter such as a tac promoter may be used.

A method for introduction of an expression vector is not particularly limited as long as DNA is introduced into a bacterium thereby. Examples thereof include a method using calcium ions (Cohen, S, N., et al., Proc. Natl. Acad. Sci., U.S.A., 69: 2110-2114, 1972) and an electroporation method.

When yeast is used as a host, Saccharomyces cerevisiae, Schizosaccharomyces pombe, Pichia pastoris, or the like can be used. In this case, a promoter is not particularly limited as long as it can be expressed in yeast. Examples thereof include a gal1 promoter, a gal10 promoter, a heat-shock protein promoter, an MFα1 promoter, a PHO5 promoter, a PGK promoter, a GAP promoter, an ADH promoter, and an AOX1 promoter.

A method for introducing a recombinant vector into yeast is not particularly limited as long as DNA is introduced into yeast thereby. Examples thereof include the electroporation method (Becker, D. M., et al., Methods. Enzymol., 194: 182-

187, 1990), the spheroplast method (Hinnen, A. et al., Proc. Natl. Acad. Sci., U.S.A., 75: 1929-1933, 1978), and the lithium acetate method (Itoh, H., J. Bacteriol., 153: 163-168, 1983).

A host microorganism may comprise at least 1 endogenous gene selected from among the "genes involved in 2-propanol biosynthesis" described above. In such a case, an endogenous gene selected from among the genes involved in 2-propanol biosynthesis may be introduced.

2-Butanol Production

2-Butanol biosynthesis proceeds, in addition to 2-propanol biosynthesis, by culturing the aforementioned microorganism into which "the acetoacetyl-CoA synthase gene" and "the genes involved in 2-propanol biosynthesis" have been introduced in a medium containing carbon sources such as glucose. In general, biosynthesis of butanol from acetoacetyl-CoA necessitates enzymes involved in butanol biosynthesis to function. Examples of such enzymes include β-hydroxybutyryl-CoA dehydrogenase that synthesizes 3-hydroxybutyl-CoA using acetoacetyl-CoA as a substrate, 3-hydroxybutyryl-CoA dehydratase that synthesizes crotonyl-CoA using 3-hydroxylbutyl-CoA as a substrate, butyryl-CoA dehydrogenase that synthesizes butyryl-CoA using crotonyl-CoA as a substrate, butylaldehyde dehydrogenase that synthesizes butylaldehyde using butyryl-CoA as a substrate, and butanol dehydrogenase that synthesizes butanol using butylaldehyde as a substrate. Although such enzymes involved in butanol biosynthesis have not been introduced so as to function in the present invention, 2-butanol is biosynthesized by microorganisms into which "the acetoacetyl-CoA synthase gene" and "the genes involved in 2-propanol biosynthesis" have been introduced.

Further, conditions for culturing a microorganism into which the aforementioned "acetoacetyl-CoA synthase gene" and "the genes involved in 2-propanol biosynthesis" have been introduced are not particularly limited. Therefore, culture can be conducted under general conditions, except for cases involving anaerobic conditions, when a medium appropriate for maintaining auxotrophy and the drug resistance of a host microorganism is used.

Since synthesized butanol is present in a medium, butanol can be obtained from a supernatant fraction after separation of cells from a medium by means of centrifugation or the like. For example, butanol can be isolated from a supernatant fraction by adding organic solvents such as ethyl acetate and methanol to such supernatant fraction and thoroughly agitating the mixture. The mixture is separated into an aqueous phase and a solvent phase, and butanol can then be extracted from the solvent phase.

EXAMPLES

The present invention is hereafter described in greater detail with reference to the following examples, although the technical scope of the present invention is not limited thereto.

Example 1

Preparation of *Clostridium acetobutylicum* Genomic DNA

The *Clostridium acetobutylicum* ATCC (824) strain was subjected to anaerobic culture at 30° C. for 2 days in 3 ml of a *Clostridium* enrichment medium (Difco) in accordance with a conventional technique. Genomic DNA was prepared from 1.5 ml of the culture solution with the use of a genomic DNA preparation kit (Gentra Puregene Yeast/Bact. kit, QIAGEN).

<Preparation of pT7Blue-CAC2873>

The thiA gene, which is a thiolase gene derived from *Clostridium acetobutylicum*, was cloned in the manner described below. First, the following primers were used for PCR.

```
CAC2873-F:
                                    (SEQ ID NO: 7)
5'-ATG AAA GAA GTT GTA ATA GCT AGT GCA G-3'

CAC2873-R:
                                    (SEQ ID NO: 8)
5'-CTA GCA CTT TTC TAG CAA TAT TGC TG-3'
```

The genomic DNA (0.1 μg) of the *Clostridium acetobutylicum* ATCC (824) strain prepared above was used as a template for PCR. In addition, each primer of the above primer pair was used in an amount of 50 μmol. A reaction solution (50 μl) comprising 1×Pfu Ultra II reaction buffer (Stratagene) containing dNTP (10 nmol) and Pfu Ultra II fusion HS DNA polymerase (Stratagene) (1 μl) was prepared. The conditions of PCR thermal cycles were as follows: 95° C. for 5 minutes; 30 cycles of 95° C. for 30 seconds, 60° C. for 30 seconds, and 72° C. for 3 minutes; and 72° C. for 3 minutes. Further, the resulting solution was stored as a stock solution at 4° C. after the completion of the reaction.

A fragment amplified by PCR (approximately 1.2 kb) was subjected to blunt-end cloning into a pT7-Blue vector with the use of a Perfectly Blunt Cloning Kit (Novagen). The cloned sequence was subjected to sequencing, and thus the sequence was confirmed to correspond to the thiA gene of the *Clostridium acetobutylicum* ATCC (824) strain. The resulting plasmid was designated as pT7Blue-CAC2873.

<Preparation of pCDFDuet-thiA>

An expression vector for causing expression of the above thiA gene in *Escherichia coli* was constructed in the manner described below. First, PCR was carried out with the use of the following primers.

```
acat-NdeI-F:
                                    (SEQ ID NO: 9)
5'-AAA CAT ATG AAA GAA GTT GTA ATA GC-3' acat-XhoI-R:
                                    (SEQ ID NO: 10)
5'-AAA CTC GAG CTA GCA CTT TTC TAG CAA T-3'
``` pT7Blue-CAC2873 prepared above was used as a template for PCR. In addition, each primer of the above primer pair was used in an amount of 10 pmol. A reaction solution (50 μl) comprising 1×Pfu Ultra™II reaction buffer (Stratagene) containing dNTP (12.5 nmol) and a Pfu Ultra™II fusion HS DNA polymerase (Stratagene) (1 μl) was prepared. The conditions of PCR thermal cycles were as follows: 95° C. for 2 minutes; 5 cycles of 95° C. for 20 seconds, 43° C. for 20 seconds, and 72° C. for 40 seconds; 30 cycles of 95° C. for 20 seconds, 50° C. for 20 seconds, and 72° C. for 40 seconds; and 72° C. for 3 minutes. Further, the resulting solution was stored as a stock solution at 4° C. after the completion of the reaction.

A DNA fragment amplified via PCR (approximately 1.2 bp) was purified with a MinElute PCR Purification Kit and cloned into a pCR-Blunt II-Topo vector with the use of a Zero Blunt TOPO PCR Cloning Kit. The resulting vector was designated as pCR-Blunt II-TOPO-thiA. pCR-Blunt II-TOPO-thiA was cleaved with NdeI and XhoI. A DNA fragment (approximately 1.2 Kbp) was purified via agarose gel electrophoresis and then inserted into the NdeI-XhoI site of pCDF-Duet (Novagen). The obtained plasmid was designated as pCDFDuet-thiA.

<Preparation of pCDFDuet-orfN>

The acetoacetyl-CoA synthase gene derived from *Clostridium acetobutylicum* and capable of synthesizing acetoacetyl-CoA from malonyl-CoA and acetyl-CoA was cloned in the manner described below. At the outset, PCR was carried out with the use of the following primers.

```
OrfN-NdeI-F:
                                            (SEQ ID NO: 11)
5'-AAA CAT ATG ACC GAC GTC CGA TTC CGC AT 3'

OrfN-XhoI-R:
                                            (SEQ ID NO: 12)
5'-AAA CTC GAG TTA CCA CTC GAT CAG GGC GA 3'
``` pHISORFn (20 ng) was used as a template for PCR. pHISORFn described in JP Patent Publication (Kokai) No. 2008-61506 A was used. In addition, each primer of the above primer pair was used in an amount of 15 pmol. A reaction solution (50 μl) comprising 1× PrimeSTAR GC Buffer (Mg$^{2+}$ plus) (TAKARA Bio Inc.) containing dNTP (10 nmol) and PrimeSTAR HS DNA Polymerase (TAKARA Bio Inc.) (0.5 μl) was prepared. PCR was carried out with the following thermal cycle conditions: 94° C. for 1 minute; 5 cycles of 98° C. for 10 seconds, 53° C. for 5 seconds, and 72° C. for 1 minute; 30 cycles of 98° C. for 10 seconds, 60° C. for 5 seconds, and 72° C. for 1 minute; and 72° C. for 5 minutes. Further, the resulting solution was stored as a stock solution at 4° C. after the completion of the reaction.

A DNA fragment amplified via PCR (approximately 1 Kbp) was purified with a MinElute PCR Purification Kit and cloned into a pCR-Blunt II-Topo vector with the use of a Zero Blunt TOPO PCR Cloning Kit. The obtained vector was designated as pCR-Blunt II-TOPO-orfN. pCR-Blunt II-TOPO-orfN was cleaved with NdeI and XhoI. A DNA fragment (approximately 1 Kbp) was purified via agarose gel electrophoresis and then inserted into the NdeI-XhoI site of pCDF-Duet (Novagen). The obtained plasmid was designated as pCDFDuet-orfN.

<Construction of pETDuet-ctfAB>

The ctfA gene and the ctfB gene, which are the acetoacetyl-CoA transferase genes derived from *Clostridium acetobutylicum*, were cloned. At the outset, PCR was carried out using the genomic DNA prepared in the above-described manner as a template. PCR was carried out with the use of PfuUltra II fusion HS DNA polymerase (STRATAGEN) and the primers shown below. (The underlined portions are restriction enzyme sites.)

```
ctfAB-NdeI-F:
                                            (SEQ ID NO: 13)
5'-ATT CAT ATG AAC TCT AAA ATA ATT AGA TTT
GAA AAT TTA AGG TC-3' ctfAB-NdeI-R:
                                            (SEQ ID NO: 14)
5'-AGA CTC GAG CTA AAC AGC CAT GGG TCT AAG-3'
```

The composition of the reaction solution used for PCR is as follows.

TABLE 1

| Composition of reaction solution | Total volume (50 μl) |
|---|---|
| Genomic DNA of *Clostridium* (0.4 μg/μl) | 1 μl (final 0.4 μg) |
| PfuUltra II fusion HS DNA polymerase | 1 μl |
| 10× PfuUltra II reaction buffer | 5 μl |
| dNTP Mix (2.5 mM each dNTP) | 5 μl (final 0.25 mM each dNTP) |
| ctfAB-NdeI-F (10 μM) | 1 μl |
| ctfAB-NdeI-R (10 μM) | 1 μl |
| Sterilized water | 36 μl |

The conditions of PCR thermal cycles were as follows: 95° C. for 2 minutes; 30 cycles of 95° C. for 30 seconds, 54.8° C. for 30 seconds, and 72° C. for 2 minutes; and 72° C. for 7 minutes. Further, the resulting solution was stored as a stock solution at 4° C. after the completion of the reaction.

PCR was carried out under the conditions described above (with an Eppendorf machine), and an amplified 1,324-bp fragment was separated via 0.8% agarose gel electrophoresis. The fragment was purified with the use of the QIAquick Gel Extraction Kit (QIAGEN) and then digested with NdeI and XhoI. After the resultant was further purified using the QIAquick PCR Purification Kit (QIAGEN), the purified fragment was inserted into the NdeI/XhoI site of pETDuet-1 (Merck). The resulting sequence was subjected to sequencing to confirm that a plasmid of interest had been prepared. The thus-obtained plasmid was designated as pETDuet-ctfAB.

<Construction of pETDuet-ADC>

The adc gene, which is the acetoacetic acid decarboxylase gene derived from *Clostridium acetobutylicum*, was cloned. At the outset, PCR was carried out using the genomic DNA prepared in the above-described manner as a template. PCR was carried out with the use of PfuUltra II fusion HS DNA polymerase (STRATAGEN) and the primers shown below. (The underlined portions are restriction enzyme sites.)

```
adc-SalI-F:
                                            (SEQ ID NO: 15)
5'-CAC GTC GAC AAG GAG ATA TAA TGT TAA AGG ATG
AAG TAA TTA AAC A-3' adc-NotI-R:
                                            (SEQ ID NO: 16)
5'-CAC GCG GCC GCT TAC TTA AGA TAA TCA TAT ATA
ACT TCA GC-3'
```

The composition of the reaction solution used for PCR is as follows.

TABLE 2

| Composition of reaction solution | Total volume (100 μl) |
|---|---|
| Genomic DNA of *Clostridium* (0.4 μg/μl) | 2 μl (final 0.8 μg) |
| PfuUltra II fusion HS DNA polymerase | 2 μl |
| 10× PfuUltra II reaction buffer | 10 μl |
| dNTP Mix (2.5 mM each dNTP) | 10 μl (final 0.25 mM each dNTP) |
| adc-SalI-F (10 μM) | 2 μl |
| adc-SalI-R (10 μM) | 2 μl |
| Sterilized water | 62 μl |

The conditions of PCR thermal cycles were as follows: 95° C. for 2 minutes; 30 cycles of 95° C. for 20 seconds, 54.8° C. for 20 seconds, and 72° C. for 3 minutes; and 72° C. for 3 minutes. Further, the resulting solution was stored as a stock solution at 13° C. after the completion of the reaction.

PCR was carried out under the conditions described above (with an Eppendorf machine), and an amplified 735-bp fragment was separated via 1% agarose gel electrophoresis. The fragment was purified with the use of the QIAquick Gel Extraction Kit (QIAGEN) and then digested with SalI and NotI. After the resultant was further purified using the QIAquick PCR Purification Kit (QIAGEN), the purified fragment was inserted into the SalI/NotI site of pETDuet-1 (Merck). The resulting sequence was subjected to sequencing to confirm that a plasmid of interest had been prepared. The thus-obtained plasmid was designated as pETDuet-ADC.

<Construction of pETDuet-ADC-ctfAB>

An expression vector for causing expression of the ctfA gene, the ctfB gene, and the adc gene in *Escherichia coli* was constructed in the manner described below. At the outset, pETDuet-ADC prepared above was digested with SalI and NotI, an amplified 753-bp fragment containing the adc gene was separated via 0.8% agarose gel electrophoresis, and the fragment was purified with the use of the QIAquick Gel Extraction Kit (QIAGEN). In addition, pETDuet-ctfAB prepared above was digested with SalI and NotI, and the resulting 6,677-bp fragment was ligated to the fragment obtained above. The resulting vector was designated as pETDuet-ADC-ctfAB.

<Construction of pCOLADuet-PDH>

The pdh gene, which is the isopropanol dehydrogenase gene derived from *Clostridium beijerinckii*, was cloned.

Based on the nucleotide sequence of the pdh gene derived from *Clostridium beijerinckii* NRRL B593 registered in the GenBank, a fragment was first designed so as to realize a high appearance frequency of the rare codon in *Saccharomyces cerevisiae* contained in such nucleotide sequence. In this example, a nucleotide fragment comprising the designed nucleotide sequence was synthesized (SEQ ID NO: 17). The synthetic DNA sequence GGGGTTTCCGCGGTCTAGAGCCACC (SEQ ID NO: 18) was added to the untranslated region located upstream of the synthesized pdh gene and the synthetic DNA sequence GGATCCGTCGACGGGG (SEQ ID NO: 19) was added to the untranslated region located downstream thereof. The resulting plasmid was designated as pCR2.1-iPDH.

With the use of pCR2.1-iPDH as a template, PCR was carried out in the manner described below. PCR was carried out with the use of PfuUltra II fusion HS DNA polymerase (STRATAGEN) and the primers shown below (the underlined portions are restriction enzyme sites).

```
PDH-EcoRI-F:
                                  (SEQ ID NO: 20)
5'-GGA ATT CCA TGA AAG GTT TCG CAA TGT T-3'

PDH-PstI-R:
                                  (SEQ ID NO: 21)
5'-AAC TGC AGA ACC AAT GCA TTG GTT ACA AAA
TGA CTA CGG-3'
```

The composition of the reaction solution used for PCR is as follows.

TABLE 3

| Composition of reaction solution | Total volume (50 μl) |
|---|---|
| pCR2.1-iPFH (0.36 μg/μl) | 1 μl (final 0.36 μg) |
| PfuUltra II fusion HS DNA polymerase | 1 μl |
| 10× PfuUltra II reaction buffer | 5 μl |
| dNTP Mix (2.5 mM each dNTP) | 5 μl |
|  | (final 0.25 mM each dNTP) |
| PDH-EcoRI-F (10 μM) | 1 μl |
| PDH-EcoRI-R (10 μM) | 1 μl |
| Sterilized water | 36 μl |

The conditions of PCR thermal cycles were as follows: 95° C. for 2 minutes; 30 cycles of 95° C. for 30 seconds, 50° C. for 30 seconds, and 72° C. for 2 minutes; and 72° C. for 7 minutes. Further, the resulting solution was stored as a stock solution at 4° C. after the completion of the reaction.

PCR was carried out under the conditions described above (with an Eppendorf machine), and an amplified 1,056-bp fragment was separated via 0.8% agarose gel electrophoresis. The cleaved fragment was purified using the MiniElute Gel Extraction Kit (QIAGEN) and digested with EcoRI and PstI. After the resultant was purified using the QIAquick PCR Purification Kit (QIAGEN), the purified fragment was inserted into the EcoRI/PstI site of pCOLADuet-1 (Merck). The resulting sequence was subjected to sequencing to confirm that a plasmid of interest had been prepared. The thus-obtained plasmid was designated as pCOLADuet-PDH.

<Preparation of Recombinant *Escherichia coli*>

The *E. coli* BL21 (DE3) strains (TAKARA Bio Inc.) were transformed with pCDFDuet-thiA, pCDFDuet-orfN, pETDuet-ADC-ctfAB, and pCOLADuet-PDH prepared above in combinations A to F shown in Table 4. The resulting recombinant *E. coli* strains were designated as A/BL21, B/BL21, C/BL21, D/BL21, E/BL21, and F/BL21, respectively.

TABLE 4

|  | A | B | C | D | E | F |
|---|---|---|---|---|---|---|
| pCDFDuet-thiA |  |  | + |  | + |  |
| pCDFDuet-orfN |  |  |  | + |  | + |
| pETDuet-ADC-ctfAB | + | + | + | + | + | + |
| pCOLADuet-PDH |  | + |  |  | + | + |

When culturing the resulting recombinant *E. coli* strains, a trace element solution having the composition below was prepared.

TABLE 5

| Composition of 1 litter trace element solution | |
|---|---|
| Reagent | 5M HCl (final concentration) |
| FeSO$_4$•7H$_2$O | 40.0 g |
| MnSO$_4$•H$_2$O | 10.0 g |
| Al$_2$(SO$_4$)$_3$ | 28.3 g |
| CoCl$_2$•6H$_2$O | 4.0 g |
| ZnSO$_4$•7H$_2$O | 2.0 g |
| Na$_2$MoO$_4$•2H$_2$O | 2.0 g |
| CuCl$_2$•2H$_2$O | 1.0 g |
| H$_3$BO$_4$ | 0.5 g |

SD-7 medium was prepared in the following manner. NH$_4$Cl (7.0 g), 1.5 g of KH$_2$PO$_4$, 1.5 g of Na$_2$HPO$_4$, 0.35 g of K$_2$SO$_4$, 0.17 g of MgSO$_4$.7H$_2$O, 5.0 g of yeast extract (Difco), and 0.8 ml of the trace element solution were dissolved in 0.8 litter of deionized water, and the pH was adjusted to 7.0 with 5M NH$_4$OH. The total amount of the medium was filled up to 1 liter with deionized water, and the resultant was sterilized in an autoclave.

Further, SD-8 medium was prepared in the following manner. NH$_4$Cl (7.0 g), 7.5 g of KH$_2$PO$_4$, 7.5 g of Na$_2$HPO$_4$, 0.85 g of K$_2$SO$_4$, 0.17 g of MgSO$_4$.7H$_2$O, 10.0 g of yeast extract (Difco), and 0.8 ml of the trace element solution were dissolved in 1 liter of deionized water, and the resulting solution was sterilized in an autoclave.

When the above recombinant *E. coli* strains were cultured in SD-7 or SD-8 medium, further, antibiotics shown in the table below were added according to need. In the table 6, "Amp" represents ampicillin, "Km" represents kanamycin (SIGMA), "Str" represents streptomycin, and "Tet" represents tetracycline.

TABLE 6

| Recombinant E. coli strains | Antibiotics (final concentration) |
| --- | --- |
| A/BL21 | 50 μg/ml Amp |
| B/BL21 | 50 μg/ml Amp, 50 μg/ml Km |
| C/BL21 | 50 μg/ml Amp, 50 μg/ml Str |
| D/BL21 | 50 μg/ml Amp, 30 μg/ml Str |
| E/BL21 | 50 μg/ml Amp, 50 μg/ml Str, 30 μg/ml Km |
| F/BL21 | 50 μg/ml Amp, 50 μg/ml Str, 30 μg/ml Km |

Single colonies of the obtained recombinant E. coli strains were inoculated in 5 ml of SD-7 medium containing 2% (final concentration) glucose (Wako Pure Chemical Industries, Ltd.) and the culture was incubated at 37° C. overnight. The culture (500 μl) was transferred into a 500 ml Erlenmeyer flask with buffer having 50 ml of SD-8 medium containing 2% (final concentration) glucose and the flask was shaked rotationally at 37° C. and 130 rpm. After IPTG (final concentration: 0.1 mM) was added at O.D. 600 of 1.0 or lower, a portion of culture solution (5 ml) was periodically dispensed into a screw-capped test tube (0, 3, 6, 9, 24, 30, and 48 hours after IPTG). The resultant was then stored at −30° C. Glucose was further added to a final concentration of 2% therein 24 hours after the addition of IPTG.

Thereafter, the culture solution stored at −30° C. was thawed at room temperature. After the broth was thoroughly suspended with a vortex, 1 ml of the culture solution was transferred into an Eppendorf tube, which had been weighed in advance, and centrifugation was carried out using a small refrigerated centrifuge (TOMY) at 13,000 rpm and 4° C. for 10 minutes. The Eppendorf tube from which the supernatant had been removed was dryed out with SpeedVac (SAVANT) for about 4 hours. Thereafter, the Eppendorf tube was weighed, the predetermined weight was subtracted therefrom, and the obtained value was designated as the dry cell weight.

The screw-capped test tube containing 4 ml of the remaining culture solution was subjected to centrifugation using a high-capacity benchtop centrifuge (LC-230, TOMY) at 1,000 g at room temperature for 5 minutes. The supernatant (2 ml) was transferred into a 20-ml headspace crimp vial, the vial was capped, and the vial was then transferred into a warm bath at 60° C. Thereafter, 2-butanol and other components were subjected to analysis via GC-MS/HSS.

GC-MS/HSS was carried out using the HP6890/5973/7694 GC-MS/HSS system (Hewlett-Packard). The J&W DB-624 column (0.32 mm×60 m; film thickness: 1.8 μm) was used, and analysis was carried out under the following conditions.
<GC/MS Analysis Conditions>
[Inlet Parameters]
Inlet temperature: 260° C.
Split ratio: 1/20
Carrier gas: Helium gas (1.0 ml/minute)
[Oven Heating Conditions]
Heating at 40° C. for 5 minutes
Heating to 75° C. at 5° C./minute
Heating to 260° C. at 100° C./minute
[Detector Conditions]
Detector temperature: 260° C.
<Headspace Sampler Conditions>
[Zoom Temp.]
Oven: 60° C.
Loop: 150° C.
Transfer line: 200° C.
[Event Time]
GC cycle time: 35 minutes
Vial EQ time: 15 minutes
Pressuriz. time: 0.5 minutes
Loop fill time: 0.2 minutes
Loop EQ time: 0.2 minutes
Inject time: 1.0 minute
[Vial Parameters]
Shake: HIGH
[Other Conditions]
Vial pressurization: 15 psi
<Standard Substance>
Ethanol (density: 0.789)
Acetone (density: 0.789)
Isopropanol (density: 0.784)
2-Butanol (density: 0.808)
Acetic acid (density: 1.05)

Figure 2:
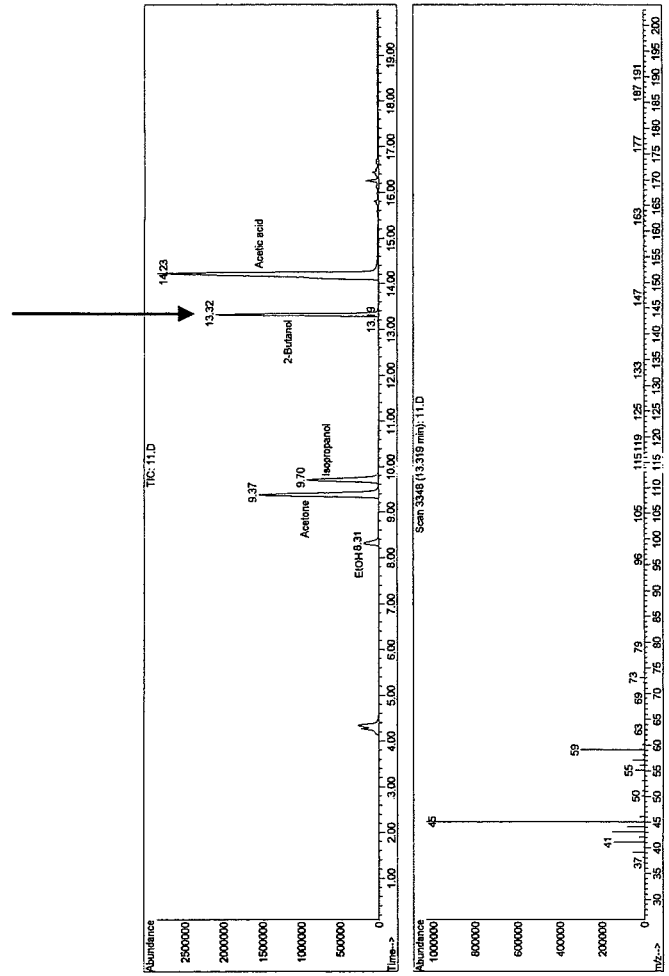
FIG. 2 is a characteristic diagram showing the results of GC-MS analysis of standard substances.

Concentrations of the five above standard substances were adjusted to adequate levels, the percent concentrations (v/v) were determined based on the calibration curve, and the weight concentrations were calculated from the value of density. FIG. 1 shows the GC/MS analysis of the culture solution of the recombinant E. coli E/BL21 strains. FIG. 2 shows the GC/MS analysis of the standard substances described above. As is apparent from FIG. 1, such strains mainly produce isopropanol, and the peak is observed at a retention time of 13.30 minutes. 2-Butanol, which was analyzed as the standard substance shown in FIG. 2, appears as a mass fragment pattern at a retention time of 13.32 minutes. It was thus concluded that the recombinant E. coli E/BL21 strains produce significant amounts of 2-butanol.

The amounts of 2-butanol produced by the recombinant E. coli strains obtained in this example are summarized in Table 7.

TABLE 7

| Strain | Cultivation time (hours) | Amount of production (mg/l) |
| --- | --- | --- |
| BL21 | 30 | 0.00 |
| A/BL21 | 30 | 0.00 |
| B/BL21 | 30 | 0.00 |
| C/BL21 | 30 | 0.00 |
| D/BL21 | 30 | 0.00 |
| E/BL21 | 30 | 3.74 |
| F/BL21 | 30 | 2.47 |

Based on the results, it was confirmed that the recombinant strain in which an acetoacetyl-CoA synthase gene, such as the thlA or ORF-n gene, was expressed in addition to the genes involved in 2-propanol biosynthesis (i.e., the ctfAB gene, the adc gene, and the pdh gene) would produce 2-butanol.

Figure 3:
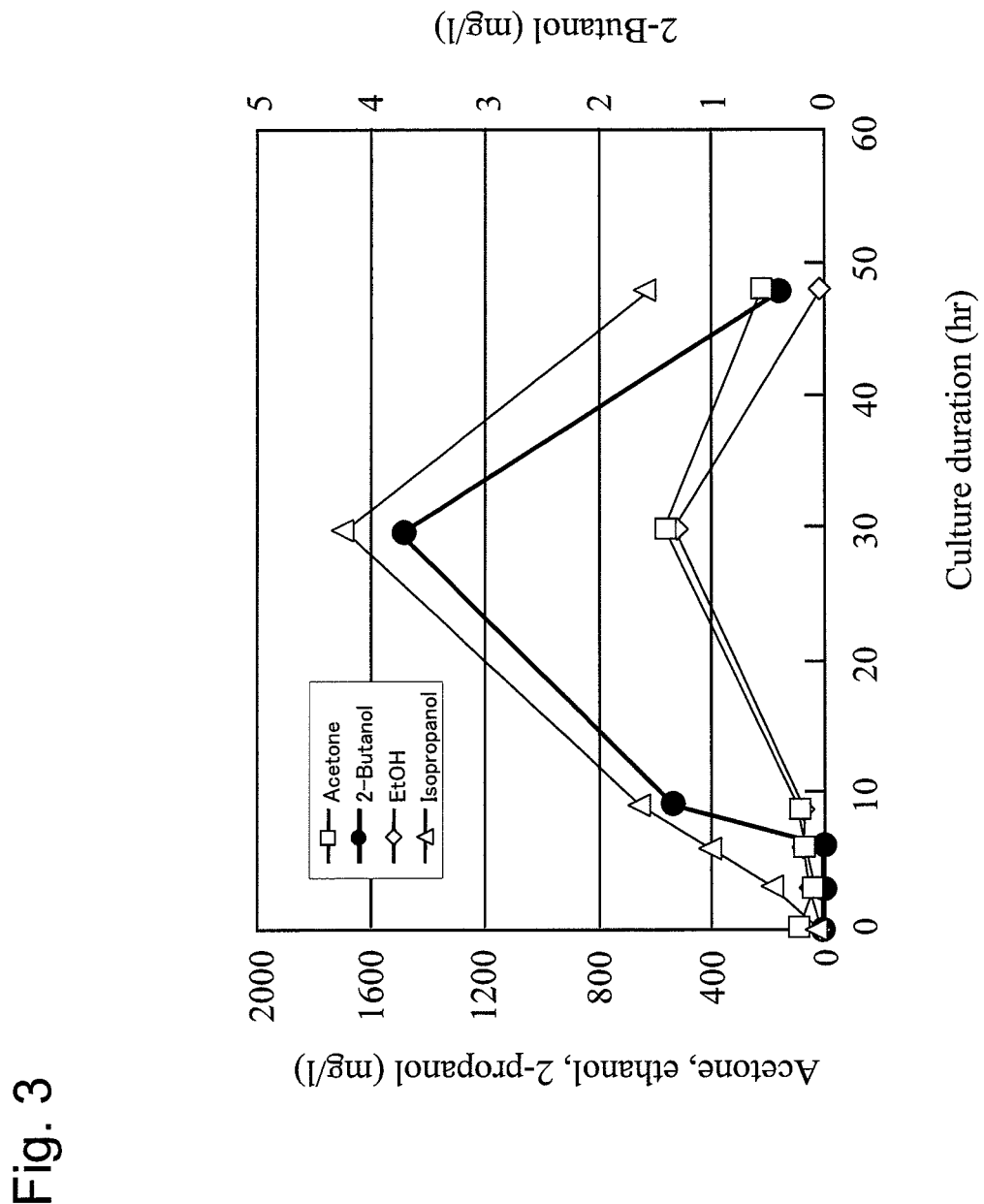
FIG. 3 is a characteristic diagram showing the results of quantification of the amounts of 2-butanol and other substances produced by the recombinant *E. coli* E/BL21 strain.

FIG. 3 shows the production of acetone, ethanol, 2-butanol, and 2-propanol in the recombinant E. coli E/BL21 strain classified as E. coli B strain. As is apparent from FIG. 3, the recombinant E. coli E/BL21 strain is capable of producing 2-butanol, even though it does not express the gene involved in butanol biosynthesis.

Example 2

In Example 2, the E. coli NovaBlue (DE3) strain classified as E. coli K strain was used, and a recombinant E. coli strain (i.e., the recombinant E. coli E/NB strain) in which the thlA gene was expressed in addition to the genes involved in 2-butanol biosynthesis (i.e., the ctfAB gene, the adc gene and the pdh gene) was prepared. The resulting recombinant E. coli strain was cultured in the same manner as in Example 1 and the volatile compounds of the culture solution were analyzed. The results thereof are shown in FIG. 4.

Figure 4:
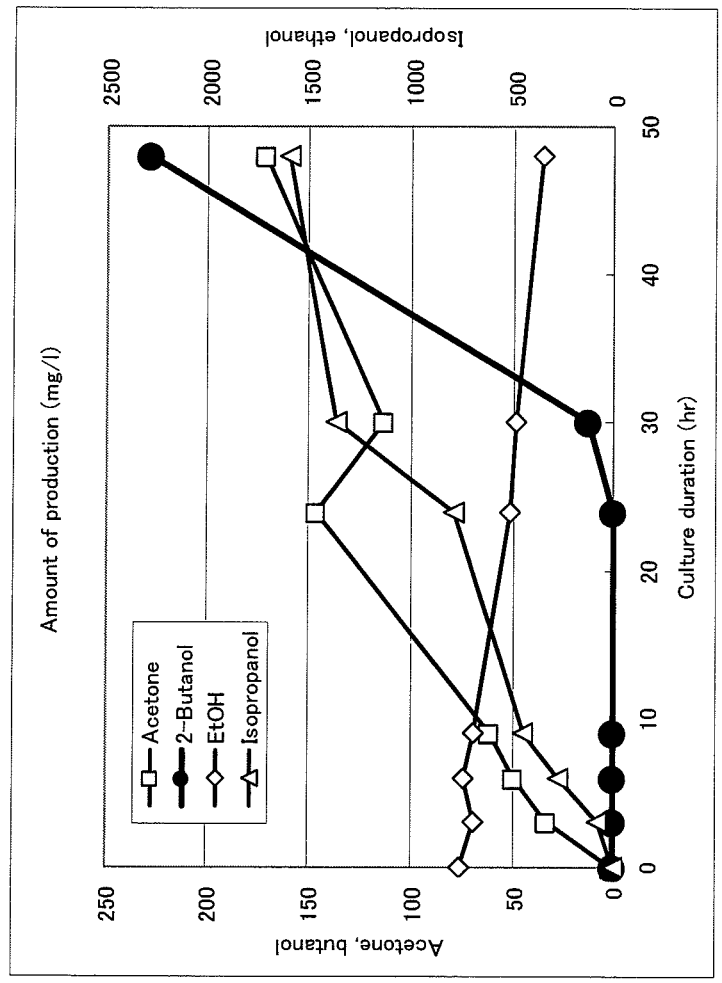
FIG. 4 is a characteristic diagram showing the results of quantification of the amounts of 2-butanol and other substances produced by the recombinant E/NB strain.

As is apparent from FIG. 4, the recombinant *E. coli* E/NB strain prepared in Example 2 is capable of producing 228.42 mg/l of 2-butanol 48 hours after the initiation of culture. Also, the recombinant *E. coli* E/NB strain was found to be remarkably superior to the recombinant *E. coli* strain prepared in Example 1 in terms of the amount of 2-butanol produced. The results indicate that a recombinant *E. coli* strain that is excellent in 2-butanol productivity can be prepared with the use of an *E. coli* K strain as a host microorganism.

The invention claimed is:

1. A method for producing 2-butanol comprising culturing in a culture medium containing a carbon source, a recombinant microorganism into which an acetoacetyl-CoA synthase gene, the acetoacetyl-CoA transferase gene, the acetoacetic acid decarboxylase gene, and the isopropanol dehydrogenase gene have been introduced and obtaining 2-butanol from the culture product.

2. The method for producing 2-butanol according to claim 1, wherein the acetoacetyl-CoA synthase gene encodes an enzyme that catalyzes a reaction that converts two acetyl-CoA molecules into acetoacetyl-CoA.

3. The method for producing 2-butanol according to claim 2, wherein the acetoacetyl-CoA synthase gene is the thiolase gene (the thlA gene) derived from *Clostridium acetobutylicum*.

4. The method for producing 2-butanol according to claim 3, wherein the acetoacetyl-CoA synthase gene encodes a protein comprising the amino acid sequence of SEQ ID NO: 2 or a protein comprising an amino acid sequence having 80% or higher identity to the amino acid sequence of SEQ ID NO: 2 and having a function of synthesizing acetoacetyl-CoA from two acetyl-CoA molecules.

5. The method for producing 2-butanol according to claim 1, wherein the acetoacetyl-CoA synthase gene encodes an enzyme that catalyzes a reaction that converts acetyl-CoA and malonyl-CoA into acetoacetyl-CoA.

6. The method for producing 2-butanol according to claim 5, wherein the acetoacetyl-CoA synthase gene is a gene (the orfN gene) derived from a *Streptomyces* microorganism.

7. The method for producing 2-butanol according to claim 6, wherein the acetoacetyl-CoA synthase gene encodes a protein comprising the amino acid sequence of SEQ ID NO: 1 or a protein comprising an amino acid sequence having 90% or higher identity to the amino acid sequence of SEQ ID NO: 1 and having a function of synthesizing acetoacetyl-CoA from malonyl-CoA and acetyl-CoA.

8. The method for producing 2-butanol according to claim 1, wherein the acetoacetyl-CoA transferase gene is the ctfA or ctfB gene of *Clostridium acetobutylicum*.

9. The method for producing 2-butanol according to claim 1, wherein the acetoacetic acid decarboxylase gene is the adc gene of *Clostridium acetobutylicum*.

10. The method for producing 2-butanol according to claim 1, wherein the isopropanol dehydrogenase gene is the pdh gene of *Clostridium beijerinckii*.

11. The method for producing 2-butanol according to claim 1, wherein the recombinant microorganism is obtained from an *E. coli* host strain.

12. The method for producing 2-butanol according to claim 11, wherein the *E. coli* strain is an *E. coli* K strain.

13. The method for producing 2-butanol according to claim 1, wherein the carbon source is glucose.

\* \* \* \* \*